United States Patent
Taub

(10) Patent No.: US 7,071,232 B1
(45) Date of Patent: Jul. 4, 2006

(54) SMALL MOLECULES THAT INCREASE THE CONVERSION OF FOOD TO BODY WEIGHT GAIN

(76) Inventor: Floyd E. Taub, 10610 Mantz Rd., Silver Spring, MD (US) 20903

( * ) Notice: Subject to any disclaimer, the term of this patent is extended or adjusted under 35 U.S.C. 154(b) by 954 days.

(21) Appl. No.: 09/637,917

(22) Filed: Aug. 14, 2000

Related U.S. Application Data

(63) Continuation-in-part of application No. 09/256,763, filed on Feb. 24, 1999, now Pat. No. 6,166,086.
(60) Provisional application No. 60/075,966, filed on Feb. 24, 1998, and provisional application No. 60/085,474, filed on May 14, 1998.

(51) Int. Cl.
*A61K 31/16* (2006.01)
*A61K 31/66* (2006.01)

(52) U.S. Cl. .................. 514/626; 514/616; 514/77; 514/107

(58) Field of Classification Search ................ 514/626, 514/616, 77, 107
See application file for complete search history.

(56) References Cited

U.S. PATENT DOCUMENTS 5,985,336 A * 11/1999 Evey et al. .................... 426/2

OTHER PUBLICATIONS

Medline AN 81206086, Atherton et al, Antimicrobial agents and chemotherapy, Dec. 1980, 18(6) 897–905, abstract.*

* cited by examiner

*Primary Examiner*—Rebecca Cook
(74) *Attorney, Agent, or Firm*—Judith A. Evans; Paul D. Roath

(57) ABSTRACT

The present invention relates to peptide-like compounds, e.g. aminocarboxylic acid amide derivatives, and to methods of using same in the field of general health care, for example, to improve resistance to stress, improve production of desired characteristics or useful products in animals, to increase weight gain, prevent diseases caused by pathogens, and to decrease feed efficiency. The invention has applications in the field of animal husbandry, and in treating or preventing weight loss associated with a disease in humans. It also relates to administering carbobenzoxy beta-alanyl taurine to improve feed efficiency in an animal, comprising administering to the animal an amount of carbobenzoxy beta-alanyl taurine sufficient to reduce the amount of food required to increase a unit of weight in the animal.

25 Claims, 1 Drawing Sheet

SMALL MOLECULES THAT INCREASE THE CONVERSION OF FOOD TO BODY WEIGHT GAIN

Figure 1A:
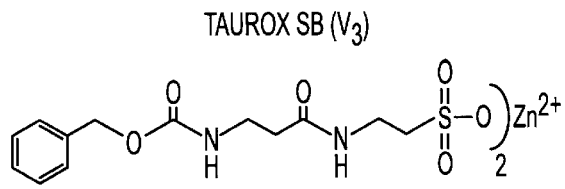

This application is a continuation in part of U.S. Ser. No. 09/256,763, filed on Feb. 24, 1999 now 6,166,086, and it claims priority to U.S. Provisional Application Nos.: 60/075,966 filed Feb. 24, 1998 and 60/085,474 filed May 14, 1998, all of which are incorporated herein by reference in their entirety.

FIELD OF THE INVENTION

The present invention relates to peptide-like compounds, e.g. aminocarboxylic acid amide derivatives, and to methods of using same in the field of general health care, for example, to improve resistance to stress, improve production of desired characteristics or useful products in animals, to increase weight gain, and to decrease feed efficiency. The invention has applications in the field of animal husbandry.

BACKGROUND OF THE INVENTION

In the area of animal husbandry, antimicrobials, including antibacterials, are used routinely for prophylaxis, chemotherapy and growth promotion. Animals receiving antibiotics in their feed, gain four to five percent more body weight than animals that do not receive antibiotics. They are important for sustainable livestock production and for the control of animal infections that could be passed on to humans. However, microbiological and clinical evidence is mounting that resistant bacteria or resistance determinants might be passed from animals to humans, resulting in human infections that are more difficult to treat. With a marked increase in the prevalence and distribution of antimicrobial-resistant infections in hospitals and the community the question has been raised as to how this escalation of resistance could have been influenced by the use of antimicrobials in livestock production.

Antimicrobials are used extensively in livestock, fish and plant production. Most are administered to livestock animals in subtherapeutic doses as growth promoters which boost the utilization of the genetic potential for growth of pigs and poultry, improve feed conversion and reduce waste production output from intensive livestock production. They are also used prophylactically to prevent diseases, for example, after commingling of animals from different farms, or among animals raised in crowded conditions with thousands of animals living under confinement on a single premises.

Antimicrobial use leads to the selection of resistant forms of bacteria in the ecosystem of use. Low level, long-term exposure to antimicrobials may have a greater selective potential than short-term, full-dose therapeutic use because full doses are more likely to kill all of the targeted bacteria in the host, making it less likely that resistant bacteria will emerge. Adverse consequences of selecting resistant bacteria include an increase in the prevalence of resistant bacteria in animals, causing diseases that won't respond to known antimicrobials; the transfer of resistant pathogens to humans via direct contact with animals, or through the consumption of contaminated food or water; the transfer of resistance genes to human bacteria; an increase in the incidence of human infections caused by resistant pathogens; and potential therapeutic failures in animals and humans.

Antibiotic resistance that arises in animal husbandry affects such zoonotic pathogens as *Salmonella serovars* and Campylobacter, both of which are associated with diarrheal diseases, and human and animal commensals such as *Escherichia coli* and enterococci. Because the human and animal microbial ecosystems are inextricably intertwined, microbial antibiotic resistance readily crosses boundaries so that antibiotics given to animals and closely related antibiotic compounds used in human therapy have been exerting selective pressure on their target bacteria for decades.

Specifically, the introduction of fluorquinolones for use in poultry caused a dramatic rise in the prevalence of fluoroquinolone-resistant *Campylobacter jejuni* isolated in live poultry, poultry meat and from infected humans. The use of avoparcin as a growth-promoting feed additive for pigs and poultry has contributed to the reservoir of transferable resistance genes to glycopeptides, including vancomycin, in the commensal enterococci of animals. Multiresistant *Escherichia coli* have been selected by use of broad spectrum antimicrobials in both livestock and humans.

The problems caused by the prolific use of a wide variety of antimicrobials in animal husbandry is a driving force for the development of antibiotic resistance in certain pathogenic bacterial species. The problems of resistance reach beyond the country of origin because meat products are traded worldwide.

Drawings

Figure 1B:
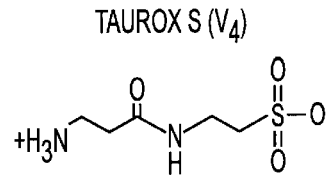
Figure 1C:
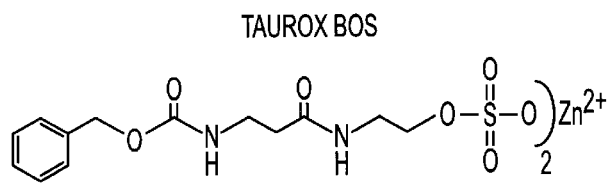
Figure 1D:
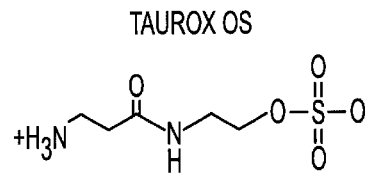
Figure 1E:
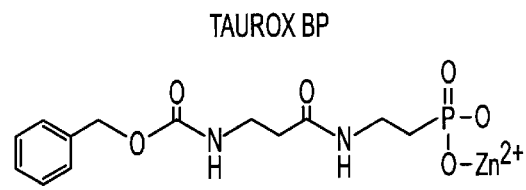
Figure 1F:
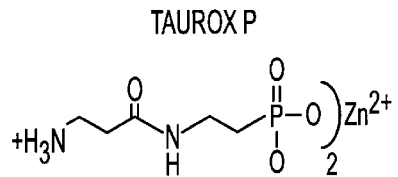
Figure 1G:
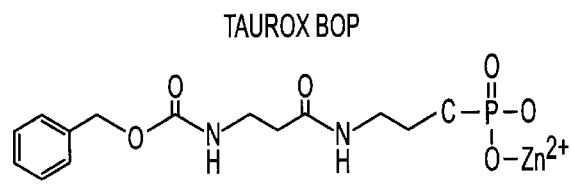
Figure 1H:
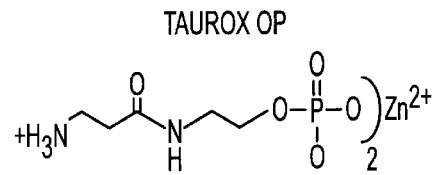

FIG. 1 shows specific TAUROX™ compounds of the invention.

SUMMARY OF THE INVENTION

The present invention is therefore directed to a nontoxic, non-antimicrobial agent that can replace or supplement the use of antibiotics in the animal husbandry of livestock animals to increase health and general well-being, productivity, feed efficiency and weight gain. The present invention is also directed to such an agent that increases the vitality of livestock animals as is indicated by their ability to withstand environmental stressors such as wide variations in temperature, food deprivation which can occur under crowded conditions, and exposure to pathogenic bacteria and viruses.

DETAILED DESCRIPTION OF THE INVENTION

In order that the present invention may be fully understood the following detailed description is set forth.

The invention describes a variety of small molecules that improve health and general well-being, increase body weight, lower feed efficiency, and help animals overcome environmental stress such as exposure to infection, temperature change, and/or food deprivation.

This invention relates to the use of many kinds of small molecules, including beta-alethine, a naturally occurring disulfide, to (1) improve general health and well being; (2) increase the ability of an animal to resist environmental stressors, including temperature change, food deprivation, and exposure to pathogenic bacteria and viruses; (3) increase the production of desired characteristics or useful products from animals, (4) increase weight gain, or (5) decrease feed efficiency in animals. The present invention also relates to the use of small molecules, including beta-alethine, to decrease mortality during shipping or transport of livestock. Other compounds, structurally similar to beta-alethine, including both disulfides and thiols, are also within the present invention. TAUROX™ compounds (described in U.S. Ser. No. 08/733,174), and small molecules having immunoregulatory isomers such as mevalonate and mevalonolactone (described in U.S. Pat. No. 5,849,777 and 5,783,594, and U.S. Serial No. 09/033,098 which are incorporated in their entirety by reference) can also be used for the various embodiments of the present invention.

Beta-alethine and TAUROX™ compounds have the Formula I:

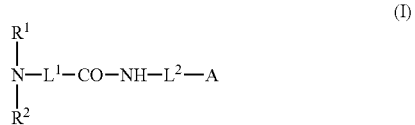
(I)

wherein:

A is a group of the formula —$PO_3H$, —$SO_3H$, —OPO—$(OH)_2$, —$OSO_2OH$, or —SH, or pharmaceutically acceptable salt thereof or physiologically hydrolyzable derivative thereof, or disulfide thereof when A is —SH. Suitable salts include sodium, potassium, calcium and zinc. Suitable hydrolyzable derivatizing groups include esters, such as substituted or unsubstituted lower alkyl (e.g. $C_1$ to $C_4$) or arylalkyl (e.g. benzyl) esters;

$R_1$ is H, a linear or branched lower alkyl, for example, a $C_1$ to $C_6$ alkyl, arylalkyl, for example, wherein the alkyl moiety is $C_1$ to $C_4$ alkyl and the aryl moiety is a substituted (eg lower alkyl or halogen) or unsubstituted phenyl group, or alkenyl (for example, $C_2$–$C_6$ alkenyl);

$R_2$ is H, a linear or branched lower alkyl, for;example, a $C_1$ to $C_6$ alkyl, an alkenyl, for example, a $C_2$–$C_6$ alkenyl, an arylalkyl, for example, wherein the alkyl moiety is a $C_1$ to $C_4$ alkyl and the aryl moiety is a substituted (eg lower alkyl or halogen) or unsubstituted phenyl group; or an acyl, for example, acetyl, benzoyl, arylsulfonyl (for example, when the aryl moiety is phenyl); a carbonate ester such as alkoxycarbonyl (e.g., $C_1$–$C_7$ alkoxy carbonyl) (for example, —$OCOC(CH_3)_3$); allyloxy carbonyl (e.g. —$OCOCH_2CH=CH_2$); cycloalkoxycarbonyl (e.g. when the ring is $C_3$–$C_8$ ($C_5$–$C_6$ being preferred) and when the alkoxy moiety is $C_1$–$C_8$) (for example —$OCOCH_2C_5H_9$); or an unsubstituted arylalkoxycarbonyl (for example —$OCOCH_2C_6H_5$) or a substituted arylalkoxycarbonyl wherein the substituent is, for example, a halogen, a nitro group, an amino group or a methoxyl group;

alternatively, $R^1$ and $R^2$ taken together form, with the nitrogen to which they are attached, a 5 to 7 membered ring (for example, $R^1$ and $R^2$ taken together can be —$(CH_2)_4$—, —$(CH_2)_5$ or —$(CH_2)_6$—); and $L^1$ and $L^2$ are hydrocarbon linking groups, for example, a linear or branched chain alkyl of the formula —$(C_nH_{2n})$—wherein n is, for example, 1 to 8 in the case of $L^1$ and 2 to 8 in the case of $L^2$ except when A is —$PO_3H$ or —$SO_3H$ in which case n can be 1–8, a cycloalkyl of 3 to 8 carbon atoms, preferably 5 or 6 carbon atoms; or an interphenytene

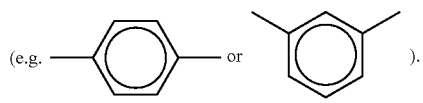

Advantageously, $L^1$ and $L^2$ are —$(C_nH_{2n})$— wherein n is 1 to 8 in the case of $L^1$ or 2 to 8 in the case of $L^2$ except when A is —$PO_3H$ or —$SO_3H$ in which case n can be 1–8 (examples of branched chain alkyls include —$CH_2CHR$—, —$CH_2CHRCH_2$—, —$CHRCH_2CH_2$—, and —$CH_2CH_2CHR$—wherein R is an alkyl group and wherein the total number of carbon atoms, including R, does not exceed 8).

A particular group of compounds of the invention is of the formula (I) wherein A, $R^1$, $R^2$, $L^1$ and $L^2$ are as defined above in said first embodiment with the proviso that when A is —$SO_3H$ or pharmaceutically acceptable salt thereof or physiologically hydrolyzable derivative thereof, one of $R^1$ and $R^2$ is H, and $L^1$ and $L^2$ are $(CH_2)_2$, then the other of $R^1$ and $R^2$ is not H.

Another particular group of compounds of the invention is of the formula (I) wherein A, $R^1$, $R^2$, $L^1$ and $L^2$, are as defined above in the first embodiment with the proviso that when A is —$SO_3H$ or pharmaceutically acceptable salt thereof or physiologically hydrolyzable derivative thereof, one of $R^1$ and $R^2$ is H, and $L^1$ and $L^2$ are $(CH_2)_2$, then the other of $R^1$ and $R^2$ is not $C_6H_5CH_2OCO$—.

A further particular group of compounds of the invention is of the formula (I) wherein A is a group of the formula —$PO_3H$ or —$OPO(OH)_2$, more particularly —$PO_3H$, or a pharmaceutically acceptable salt thereof or a physiologically hydrolyzable derivative thereof, and wherein $R^1$, $R^2$, $L^1$, and $L^2$ are as defined above in the first embodiment.

Another particular group of compounds of the invention is of the formula (I) wherein A is a group of the formula —$SO_3H$ or —$OSO_2OH$, more particularly —$OSO_2OH$, or pharmaceutically acceptable salt thereof, or physiologically hydrolyzable derivative thereof, and wherein $R^1$, $R^2$, $L^1$ and $L^2$ are as defined above in the first embodiment. The provisos above can apply to this group of compounds as well.

A further particular group of compounds of the invention is of the formula (I) wherein at least one of $R^1$ and $R^2$ is an alkyl, advantageously a lower alkyl (eg $C_1$ to $C_6$), and wherein A, $L^1$, $L^2$ and the other of $R^1$ and $R^2$ are as defined above in the first embodiment.

Another particular group of compounds of the invention is of the formula (I) wherein $R^1$ is an alkyl and $R^2$ is acyl and wherein A, $L^1$ and $L^2$ are as defined above in the first embodiment.

A further particular group of compounds of the invention is of the formula (I) wherein $L^1$ is —$(CH_2)$—and wherein A, $R^1$, $R^2$, and $L^2$ are as defined above in the first embodiment.

Yet another particular group of compounds of the invention is of the formula (I) wherein $R^1$ and $R^2$ are taken together and form, with the nitrogen to which they are attached, a 5 to 7 membered ring, and wherein A, $L^1$ and $L^2$ are as defined above in the first embodiment.

The various TAUROX™ compounds of formula I are shown in FIG. 1. They are: TAUROX™ S: Beta-alanyltaurine or Beta-alanyl-2-aminoethylsulfonic acid, TAUROX™ SB: [Zinc] Carbobenzyloxy-beta-alanyltaurine, or [Zinc] carbobenzyloxy-beta-alanyl-2-aminoethylsulfonic acid, TAUROX™ OS: Beta-alanylethanolamine 0-sulfate, TAUROX™ BOS: [Zinc] carbobenzyloxy-beta-alanylethanolamine O-sulfate, TAUROX™ OP: [ Zinc] Beta-alanylethanolamine O-phosphate, TAUROX™ BOP: [Zinc] Carbobenzyloxy-beta-alanylethanolamine O-phosphate, TAUROX™ P: [Zinc] Beta-alanyl-2-aminoethylphosphonic acid, and Tarox™ BP: [Zinc] Carbobenzyloxy-beta-alanyl-2-aminoethylphosphonic acid.

The present compounds can also be present covalently bound to proteins, for example, antigens or other immunologically active proteins, or cell targeting proteins. Such conjugates can be synthesized using techniques known in the art.

The compounds of the present invention can be prepared using, for instance, methods provided in the Examples and in U.S. Pat. No. 4,102,948 and U.S. Pat. No. 4,218,404, as appropriate.

The disulfide beta-alethine, and beta-aletheine (the corresponding thiol) have a variety of diverse effects including use as a nontoxic anti-cancer agent, the ability to delay senescence in vivo and in vitro, and to facilitate the adaptation and differentiation of cultured cells. Knight et al., U.S. Pat. No. 5,643,966, and U.S. application Ser. Nos. 08/346, 177, 08/468,043, and 08/468,041, which are incorporated herein by reference for all purposes. Beta-alethine has also been reported to be an adjuvant that stimulates antigen-specific immunoglobulin synthesis. (08/733,174 incorporated herein by reference).

In a first embodiment, it was discovered that small molecules of the present invention, enhanced the ability of animals to withstand environmental stressors. To test the effects of beta-alethine on the ability of animals to withstand environmental stress, experimental chicks received a single injection of beta-alethine on the day of the hatch, which was day one of an 18 day experiment. On day 8, a Newcastle disease live virus vaccine was administered. On Day 11, the chicks were stress by simultaneous food withdrawal, temperature extremes, and aerosol exposure to *E. coli* 19B. Temperature stress continued through day 14. On day 18, all pens of chicks, were evaluated for weight gain and feed efficiency, adjusting for dead chicks; mortality was observed throughout the study.

Beta-alethine decreased mortality as early as day seven, and mortality continued to be lower in beta-alethine-treated chicks through day 16 of the experiment in two pens and throughout the entire study in the other pen. Beta-alethine enhanced the ability of chicks to survive environmental stressors that are commonly encountered in poultry houses where chickens are commercially raised in large numbers and are therefore routinely exposed to pathogenic viruses and bacteria. It is also possible that beta-alethine's ability to act as an adjuvant to stimulate an antigen-specific immune response to pathogens may have contributed to the decrease in mortality of chicks exposed to *E. coli* antigen.

In a most preferred embodiment, approximately 50 ng/kg beta-alethine is administered to an animal to decrease mortality from environmental stressors and/or to enhance the ability of the animal to tolerate food deprivation or temperature extremes, and/or to enhance the likelihood that the animal will survive exposure to pathogenic viruses or bacteria. In another preferred embodiment, beta-alethine is administered at a dose of from about 200 pg to about 20 mg per kilogram.

It is emphasized that the small molecules in the embodiment of the present invention can be administered at any time during the life of the animal, and periodic administrations throughout the life of the animal are anticipated to achieve the optimum benefit from the drug. In one preferred embodiment, the compounds of Formula I are injected in ovo. In another embodiment, the drugs are injected shortly after hatch administered by one of a variety of routes known in the art of veterinary medicine and animal husbandry and periodically thereafter.

One embodiment of the present invention is directed to multiple administrations of Formula I compounds or other small molecules during the life of the animal. A particularly important time to administer drug is shortly before livestock animals such as cattle, pigs, sheep, fish, shrimp, shellfish and goats, are transported from one location to another in order to increase vitality of the animals and their ability to survive the stress of crowded conditions, exposure to pathogens, deprivation of food and water, and temperature changes. The use of the drugs disclosed herein to enhance the ability of an animal to withstand environmental stress includes human travel, shipment of cows, turkeys and other food or pet animals or desirable or valuable animals of all types, between sites used to rear or house them, weaning of animals including pigs, and farming of land animals and of tank and "open water" raising of fish and shellfish. It has also been discovered small molecules, including beta-alethine increase the ability of an animal to combat external stress including stress imposed by chemical agents, all types of radiation, natural toxin, and all manner of infectious agents. In addition to protecting whole animals from internal and external stress, specific organs such as brains, skin, heart, liver and other vital tissues are protected from loss of mass and the adverse effects of stress or bacterial or viral disease. Animals (including but not limited to humans, livestock animals, chickens, birds, mammals, reptiles, shrimp, fish and shellfish) are frequently exposed to normal stress of growth and development and specific stress such as viral exposure and/or bacterial exposure. It has further been discovered that the compounds disclosed herein increase body weight and lower feed efficiency (i.e., the amount of feed required for weight gain) thus multiple uses in animal husbandry, and food production are discovered. Reduction of disability, stress induced illness, weight loss is advantageous at various times including but not limited to the treatment and/or prevention of loss of weight and life when animals are shipped and stressed including human travel, shipment of cows, turkeys and other food or pet animals between sites used to rear or house them, weaning of animals including pigs, and farming of land animals and of tank and "open water" raising of fish and shellfish.

The present invention is not limited to beta-alethine; molecules that are structurally or functionally similar to beta-alethine can also be used to accomplish the objectives of the present invention. The use of disulfides, thiols, TAUROX™ compounds such as TAUROX™-SB and other amino-peptide like compounds disclosed in U.S. Ser. No. 08/733,174 which issued as U.S. Pat. No. 6,007,819, can also be used for the embodiments described herein. Small molecules having isomers such as mevalonate and mevalonolactone (described in U.S. Pat. No. 5,849,777 and 5,783,594, and U.S. Ser. No. 09/033,098 which are incorporated in their entirety by reference).

It was discovered that beta-alethine has a positive effect on weight gain and on lowering feed efficiency in animals by significantly increasing conversion of feed to weight; thus multiple uses in animal husbandry and food production are discovered. The results of one experiment using highly stressed male Peterson×Hubbard broiler chicks, show that the feed efficiency ratio of the beta-alethine-treated group was 7.9% lower relative to the negative controls. In a second study using a normal flock of Avian×Ross broiler chicks, an average decrease in feed efficiency ratios of about 4%. Therefore, another embodiment of the present invention is the use of beta-alethine or functionally or structurally similar compound, or other small molecules disclosed herein to decrease feed efficiency values.

The deliverable weight ratio is similar to feed efficiency, but it includes an adjustment for the food consumed (and wasted) by chicks that do not survive. Experimental results show that beta-alethine caused a 10.8% improvement in final deliverable weight ratio (lower values) relative to controls. Therefore, another embodiment of the present invention is the use of beta-alethine or structurally similar or functionally similar molecule, to increase deliverable weight ratios in livestock animals or other animals including birds, fish, shellfish, bovine, porcine, and goats. The compounds can also by administered to animals to increase milk production, or to enhance production of other valuable or desirable characteristics such as improving fur, hooves, feathers, and so on. The compounds, especially beta-alethine and TAUROX-SB (carbobenzoxy-beta-alanyl taurine) are useful in any animal raised as a pet or for food or to produce a desired product, including milk, wool, caviar, feathers, nails, fur, hooves. Increase products even if not increase efficiency.

In another embodiment, small molecules, including beta-alethine, are administered to humans or other animals suffering from disease-associated weight loss in order to increase weight gain and/or to improve the utilization of food by increasing the conversion of food to body weight. Such illnesses include anorexia nervosa, AIDS, cachexia, Crohn's disease, or other illnesses or situations where the patient/animal ingests less food, or absorbs the nutrients from the food less efficiently than is desired. These compounds can also be used to treat underweight animals including humans, who do not have a disease, in order to increase body weight and/or the conversion of food to body weight. The compounds can be administered for this purpose at doses ranging from the picogram range to the miligram range, as needed, up to the maximum tolerated dose. Acceptable doses can be determined using routine practices.

In one embodiment, beta-alethine is administered at relatively low doses once every 14 days or on a daily basis over extended periods of time to raise or maintain body weight, for example in relatively normal population including elderly, young or the sick. Alternatively, for example in a crisis situation, beta-alethine is administered at higher doses as needed and the amount administered is manipulated based on the response of the recipient.

The compounds of Formula I for use in the various embodiments of the present invention can be administered as needed by observing standard indicia of the progress of the disease using methods known to persons of ordinary skill in the art. The drugs are preferably administered on a daily or alternate-day regimen as described more fully below, until the lo desired results are achieved. Other regimens, such as weekly or biweekly regimens may suffice, particularly when a positive response is readily apparent. Decreases in dosages of the drugs, the frequency of administration, or both, can be made as normalization progresses. The methods of the present invention are not limited to any particular amount of the above-identified drugs, as therapeutically effective amounts can be determined by routine testing.

The compounds of the present invention are typically used in the form of a pharmaceutical composition comprising one or more compounds of Formula I, or salt or hydrolyzable derivative thereof, together with a pharmaceutically acceptable or feed acceptable diluent or carrier. The compositions of the present invention are also so formulated. The compounds may be administered topically, orally, rectally, intravaginally intravenously, intraperitoneally, subcutaneously, intramuscularly or intranasally, or by other means known in the art, as appropriate for the effect sought. The drugs can also be administered transdermally using, for example, transdermal patches or transmucosally via sprays or other application. The drugs can be present in dosage unit form, for example, as a tablet, capsule or suppository, or formulated so as to be suitable for topical application (e.g., as a gel, cream, lotion or ointment). The compounds and compositions of the present invention can also be administered in liposomes, microemulsions, sprays, or via any alternative delivery system.

Alternatively, the drugs can be present as a solution or suspension (e.g., sterile) suitable for administration by injection, inhalation, intranasally or drop wise to the eye or other sites as appropriate. The drugs of the invention can be prepared as a slow release formulation appropriate for internal or external use. Using techniques known in the art, they can also be trapped in or bound to a polymer, a solid support, a liposome or a gel.

Beta-alethine, TAUROX™ compounds and other compounds of Formula I, can be administered together with additional active agents such hormones, vitamins, cytokines, enzyme regulators, regulatory macromolecules, regulatory thiols or other small molecules.

The compounds and compositions of the present invention are suitable for therapeutic use in humans and for veterinary treatment of similar conditions affecting warm-blooded animals, such as dogs, cats, horses, birds and cattle and for reptiles, and fish. For such purposes, the compounds can be administered in an analogous amount and manner to those described above for administration to humans.

Therapeutic administration of the beta-alethine and the TAUROX™ compounds may be performed by methods known to those skilled in the art including orally, transmucosally, sublingually, parenterally, intravenous, intramuscular or subcutaneous routes, direct delivery into the tumor, direct delivery into an affected body cavity by infusion, and oral or rectal administration.

A therapeutic dose, of the compounds of Formula I for use with the methods and compositions of the present invention, is an amount that is effective to modulate cytokine production by immunocytes, or increase cytotoxic T lymphocytes, or activate T cells, or increase cellular immunity, or increase PMBC proliferation. The amount of the compounds to be used and the frequency of exposure for statistically significant effects can be readily determined by one skilled in the art and will vary with the type of disease being treated or the cell type in the case of ex vivo therapy, and the effect sought. The term "statistically significant" is well known to those skilled in the art.

Cells can be grown or stored in the presence of the compounds using any of a variety of available techniques, including growth on plastic or glass or other support (e.g., beads or hollow fibers), growth in suspension (e.g., in liquid or semisolid medium), growth in a bioreactor, or storage in a frozen or dried state. Primary cultures or serial cultures, or otherwise, can be used.

The amount of the compound of the invention to be used and the frequency of exposures or statistically significant effects can be readily determined by one skilled in the art and will vary with the cell type, the compound used and the effect sought. In determining optimum concentrations, appropriate in vitro assays are run in the femtogram/ml to hundreds of mg/ml range.

Various aspects of the present invention are described in greater detail in the non-limiting Examples that follow.

Certain of the synthetic procedures for making small molecules that can be used in the present invention are described by Knight et al, Cancer Research 54:5623 (1994) or in U.S. Pat. No. 4,218,404, U.S. Ser. No, 08/733,174, or represent modifications thereof. These references are incorporated by reference herein in their entirety. In addition, the disclosures of WO 92/00955 and PCT/US91/04725 are relevant here, including the portions therein that relate to syntheses, therapeutic regimens and cell culture treatment protocols, those regimens and protocols being applicable to the drugs of the present invention. These references are also incorporated by reference herein in their entirety.

EXAMPLES

Example I

Beta-alethine Increases Ability of Animals to Withstand Environmental Stressors

Beta-alethine was administered to young chicks prior to exposure to a series of environmental stressors that includes a live virus vaccine and challenge with the bacterial pathogen *E. coli*, to test whether beta-alethine increases the longevity and basic health of the chicks.

On day one, 300 Peterson×Hubbard male broiler chicks were randomly assigned to receive either beta-alethine only or an undisclosed positive control; or no treatment prior to exposure. On day one, experimental chicks received 2 ng per chick (approximately 50 ng/kg) s.c. beta-alethine. The positive control group received 10 µg/chick of an undisclosed compound and negative controls received no drugs. On day 8, a Newcastle disease live virus vaccine was administered by injection to both positive and negative controls and to experimental chicks. There were 45 chicks in beta-alethine pen #2 and 50 in all other pens. On Day 11, the chicks were stressed by simultaneous food withdrawal for 8 hours, temperature extremes (95° F. at 6:30 am and 68° F. at 2:30 pm), and aerosol exposure to *E. coli* 19B. Temperature stress continued through day 14. On day 18, all pens of chicks were evaluated for weight gain and feed efficiency; mortality was recorded throughout the study.

The mortality rate was lower in beta-alethine-treated chicks beginning on day 7 than in negative controls receiving no drugs (0% vs. 3%), and it continued to be lower throughout the experiment. In general, the beta-alethine groups were similar to the positive controls. Survival analysis of mortality through day 16 indicated significant differences (p=0.016) between mortality of the negative controls and the beta-alethine-treated chicks. The results show that 96% of the beta-alethine-treated group survived to day 16, compared to only 85% of the untreated control group (the negative control group). Mortality due to all causes of death through day 16 are displayed in Table I.

On days 17 and 18, 5 chicks in one beta-alethine pen died, resulting in a non-significant advantage at the end of study. We believe that there may have been a technical failure that resulted in these 5 deaths. Alternatively, it is possible that the protective effect of beta-alethine lasts about 2 weeks rather than the 18 days of the study.

A similar statistically significant (p=0.044) reduction in the number of deaths attributed to colibacillosis (i.e., *E.coli* challenge) in the beta-alethine -treated group compared to negative controls measured on day 16. Deaths were attributed to colibaccilosis if the death occurred after exposure and the air sac culture was positive. Thus, all measures of mortality were reduced by treatment with Beta-alethine. Survival in the positive control group was similar to that observed for the beta-alethine-treated group, but slightly (and nonsignificantly) worse at most time.

TABLE II

Beta-alethine (BT) Reduces All Causes of Death

| Type of Mortality | Evidence |
| --- | --- |
| Early death, prior to challenge | Nonsignificant trend (p = .2): fewer deaths in the beta-alethine group prior to day 11. (See left side of table _ |
| Death after challenge with *E. coli* | Survival analysis through day 16 p = .044 (see table I), for those with *E. coli* infections |
| Total mortality | Survival analysis through day 16 p = .016 (see table I) |

TABLE III

Survival (% Alive)

| Day | Beta-alethine | Untreated Control |
| --- | --- | --- |
| 6 | 100% | 100% |
| 8 | 100 | 96 |
| 10 | 99 | 96 |
| 12 | 98 | 96 |
| 14 | 98 | 88 |
| 16 | 96 | 85 |

Feed Efficiency and Deliverable Weight Ratio

Beta-alethine significantly increased conversion of chicken feed to chicken weight. The increased conversion is indicated by lower feed efficiency values which means that less food is needed to increase weight. Feed efficiency is an estimate of the units of food used by live chicks to produce a unit of chicken weight. In all cases, weight and food consumption is measured by weighing the whole pen and all feed. Only the dead chicks are individually weighed. F.E.= Pounds food consumed, ((total final weight of live chicks minus start weight at day 0)+total weight of dead birds. The feed efficiency calculation adds the weight of the dead chicks to the total weight of the live chicks in order to adjust for the weight of the dead chicks. The lower the feed

TABLE I

Cumulative deaths by test day 18

| Treatment (# of chicks) | # dead from all causes of death | | | | | | | | | | | day 18, # dead from *e. coli* |
| --- | --- | --- | --- | --- | --- | --- | --- | --- | --- | --- | --- | --- |
| day: | 5 | 7 | 8 | 11 | 12 | 13 | 14 | 15 | 16 | 17 | 18 | infection |
| BT (n = 50) #1 | 0 | 0 | 0 | 1 | 1 | 1 | 1 | 1 | 1 | 1 | 2 | 1 |
| BT (n = 45) #2 | 0 | 0 | 0 | 0 | 1 | 1 | 1 | 1 | 3 | 6 | 8 | 8 |
| pos. control (n = 50) | 0 | 0 | 0 | 0 | 0 | 2 | 2 | 3 | 4 | 4 | 4 | 4 |
| pos. control (n = 50) | 1 | 1 | 3 | 3 | 3 | 3 | 3 | 3 | 3 | 4 | 4 | 1 |
| neg. control (n = 50) | 0 | 1 | 1 | 1 | 1 | 5 | 5 | 5 | 5 | 5 | 5 | 4 |
| neg. control (n = 50) | 0 | 2 | 3 | 3 | 3 | 7 | 7 | 9 | 10 | 11 | 11 | 8 | n = number of chicks.

efficiency, the less food is required to produce a unit of chicken weight. The calculation does not reflect the food wasted by dead chicks, but does attempt to adjust for them. The results show that the feed efficiency of the beta-alethine-treated group was 7.9% lower relative to the negative controls, and also somewhat lower than the positive controls (Table IV).

The deliverable weight ratio was calculated because it is similar to feed efficiency, but it includes an adjustment for the food consumed (and wasted) by chicks that do not survive. D.W.=Pounds food consumed, (total final weight of live chicks minus start weight). The deliverable weight ratio includes the food consumed and the total resulting weight after including all resources. This reflects the fact that dead chicks will have consumed food and required the same initial investment of other resources as live chicks, but they do not contribute to the final deliverable pounds of chicken.

The results show that beta-alethine caused a 10.8% point improvement in final deliverable weight ratio (lower values) relative to untreated controls.

TABLE IV

Beta-alethine Improves Feed Efficiency and Deliverable Weight Ratio

| Group | Feed Efficiency | Deliverable Weight Ratio$^2$ |
|---|---|---|
| beta-alethine (#1 plus #2) | 1.298 | 1.367 |
| positive control | 1.359 | 1.403 |
| negative control | 1.409 | 1.532 |
| Beta-alethine vs negative control % improvement | 7.9% | 10.8% |

The results of this experiment shows that a single dose of 2 ng per chick (approximately 50 ng/kg) beta-alethine (BT) given subcutaneously on day one of the experiment protected against death increasing the general health and well-being of the animals as is indicated by their enhanced resistance to environmental stressors. Beta-alethine (BT) administered 5 days prior to vaccination with live Newcastle disease virus and 10 days prior to the challenge with *E. coli*, significantly decreased mortality. The beta-alethine-treated group also exhibited increased weight, a lower feed efficiency and a higher deliverable weight ratio.

Example II

A second experiment was conducted using chicks from a different breeder and exposing them to less environmental stress. Avian x Ross broiler chicks were randomly assigned to groups receiving BT or saline, either in ovo at 17 days of development (4 days before hatch) or s.c. at day of hatch, with or without additional BT fed directly in water on days 4, 8, 18 and 25. All chicks received their respective treatment again on day 14. The BT dose was with 2 pg per bird or 2 ng (approx 50 ng/kg); birds receiving additional BT in the drinking water were given 2 ng per bird. There were a total of 3840 chicks (60 per pen) in 8 experimental conditions (including controls) with 8 repetitions of each. The results through day 14, were collected before the second injections. At day 14, there was little mortality and no differences between groups on any measure except feed efficiency, which was improved in some of the BT groups. Specifically, administration of 2 ng BT in ovo resulted in significantly greater conversion of feed to weight (lower efficiency ratios). S.c. administration of 2 ng BT was also significantly better than saline given in ovo, but the difference between that group and the s.c. saline administration was not significant.

TABLE V

% Decrease in Feed Efficiency Ratios Caused by Beta-alethine

| dose per bird, and route | MEAN | Signif.* | S.D. | % decrease over saline control** saline #1 | saline #2 |
|---|---|---|---|---|---|
| saline in ovo #1 | 1.185 | d | 0.0154 | n/a | |
| 2 pg BT in ovo | 1.181 | d | 0.0133 | 0.34 | −0.34 |
| 2 ng BT in ovo | 1.147 | a*** | 0.0146 | 3.21 | 55 |
| saline sc | 1.163 | bc | 0.0157 | n/a | |
| 2 pg BT sc | 1.173 | cd | 0.0107 | −0.89 | |
| 2 ng BT sc | 1.150 | ab | 0.0105 | 1.16 | |
| saline in ovo #2 | 1.177 | cd | 0.0111 | n/a | |
| 2 ng BT in ovo + fed in water (2 ng weekly) | 1.157 | ab*** | 0.0190 | 2.39 | 1.73 |

*Note regarding stastistical significance: Means within a row without a common superscript are significantly different (P < 0.05) as determined by Least Significant Difference. The small standard deviations indicate that the mean is a good representation of the group values and that even small differences between groups are meaningful.
**Lower values for feed efficiency are more desirable, as they indicate less food is needed for weight gain. Where there are two values, the first column is Saline in ovo #1; the second is Saline in ovo #2. Groups treated s.c. have only the saline s.c. control.
***significantly different from all saline groups.

All documents cited above are hereby incorporated in their entirety by reference. The entire contents of U.S. Provisional Appln. No. 60/005,336, filed Oct. 17, 1995; and 60/075,966 and 60/085,474, are also incorporated herein in their entirety.

One skilled in the art will appreciate from a reading of this disclosure that various changes in form and detail can be made without departing from the true scope of the invention.

What is claimed is:

1. A method of lowering feed efficiency in an animal, comprising administering to the animal an amount of a compound of Formula I

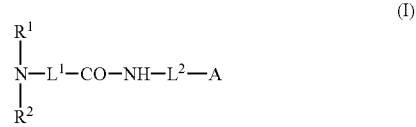

wherein:
the group A is SO$_3$H or a pharmaceutically acceptable salt thereof or physiologically hydrolyzable derivative thereof;
the group R$^1$ is H, a linear or branched lower alkyl, an arylalkyl or an alkenyl;
the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbony;
or the groups R$^1$ and R$^2$ taken together form, with the nitrogen to which to which they are attached, a 5 to 7 membered ring; and
the groups L$^1$ and L$^2$ are, independently, a hydrocarbon linking group, a cycloalkyl, or an interphenylene;
with the proviso that the compound of formula I is not beta-alethine;
which amount is sufficient to reduce the amount of food required to increase a unit of weight in the animal.

2. The method of claim 1 wherein
the group A is SO$_3$H or a pharmaceutically acceptable salt thereof or physiologically hydrolyzable (C$_1$ to C$_4$)alkyl or arylalkyl ester thereof;
the group R$^1$ is H, a linear or branched (C$_1$ to C$_6$)alkyl, a substituted or unsubstituted phenyl(C$_1$ to C$_4$)alkyl or a (C, to C$_6$)alkenyl;
the group R$^2$ is H, a linear or branched (C$_1$ to C$_6$)alkyl, a (C$_1$ to C$_6$)arylakyl, a substituted or unsubstituted (C$_1$ to C$_4$)alkenyl, acetyl, benzoyl or arylsufonyl, a (C$_1$ to C$_7$)alkoxycarbonyl, —OCOCH$_2$CH=CH$_2$, a (C$_1$ to C$_8$)cyclo(C$_1$ to C$_8$)alkoxycarbonyl, —OCOCH$_2$C$_6$H$_5$ or a substituted arylalkoxycarbonyl wherein the substituent is a halogen, a nitro group, an amino group or a methoxyl group;
or the groups R$^1$ and R$^2$ taken together form, with the nitrogen to which to which they are attached, a 5 to 7 membered ring; and
the groups L$^1$ and L$^2$ are, independently, a linear or branched chain alkyl of the formula —(C$_n$H$_{2n}$)— wherein n is 1 to 8, cycloalkyl of 3 to 8 carbon atoms, or an interphenylene.

3. A method of increasing weight gain in an animal, comprising administering to the animal an amount of a compound of Formula I

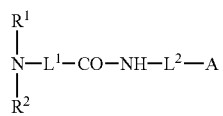

(I)

wherein:
the group A is SO$_3$H or a pharmaceutically acceptable salt thereof or physiologically hydrolyzable derivative thereof;
the group R$^1$ is H, a linear or branched lower alkyl, an arylalkyl or an alkenyl;
the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;
or the groups R$^1$ and R$^2$ taken together form, with the nitrogen to which they are attached, a 5 to 7 membered ring; and
the groups L$^1$ and L$^2$ are, independently, a hydrocarbon linking group, a cycloalkyl, or an interphenylene;
with the proviso that the compound of formula I is not beta-alethine;
which amount is sufficient to reduce the amount of food required to increase weight gain in the animal.

4. The method of claim 3 wherein
the group A is SO$_3$H or a pharmaceutically acceptable salt thereof or physiologically hydrolyzable (C$_1$ to C$_4$)alkyl or arylalkyl ester thereof;
the group R$^1$ is H, a linear or branched (C$_1$ to C$_6$)alkyl, a substituted or unsubstituted phenyl(C$_1$ to C$_4$)alkyl or a (C2 to C$_6$)alkenyl;
the group R2 is H, a linear or branched (C$_1$, to C$_6$)alkyl, a (C$_1$ to C$_6$)alkenyl, a substituted or unsubstituted phenyl(C$_1$ to C$_4$)alkyl, an acetyl, benzoyl or arylsufonyl, a (C$_1$ to C$_7$)alkoxycarbonyl, —OCOCH$_2$CH=CH$_2$, a (C$_3$ to C8)cyclo(C$_1$ to C$_8$)alkoxycarbonyl, —OCOCH$_2$C$_6$H$_5$ or a substituted arylalkoxycarbonyl wherein the substituent is a halogen, a nitro group, an amino group or a methoxyl group;
or the groups R$^1$ and R$^2$ taken together form, with the nitrogen to which they are attached, a 5 to 7 membered ring; and
the groups L$^1$ and L$^2$ are, independently, a linear or branched chain alkyl of the formula —(C$_n$H$_{2n}$)— wherein n is 1 to 8; cycloalkyl of 3 to 8 carbon atoms, or an interphenylene.

5. A method of increasing the conversion of food to body weight in an animal, comprising administering an amount of a compound of Formula I

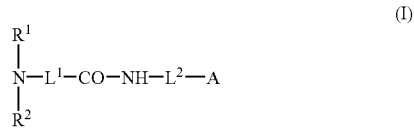

(I)

wherein:
the group A is SO$_3$H or a pharmaceutically acceptable salt thereof or physiologically hydrolyzable derivative thereof,
the group R$^1$ is H, a linear or branched lower alkyl, an arylalkyl or an alkenyl;
the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;
or the groups R$^1$ and R$^2$ taken together form, with the nitrogen to which they are attached, a 5 to 7 membered ring; and
the groups L$^1$ and L$^2$ are, independently, a hydrocarbon linking group, a cycloalkyl, or an interphenylene;
with the proviso that the compound of formula I is not beta-alethine;
which amount is sufficient to increase conversion of food to body weight.

6. The method of claim 5 wherein
the group A is SO$_3$H or a pharmaceutically acceptable salt thereof or physiologically hydrolyzable (C$_1$ to C$_4$)alkyl or arylalkyl ester thereof,
the group R$^1$ is H, a linear or branched (C$_1$ to C$_6$)alkyl, a substituted or unsubstituted phenyl(C$_1$ to C$_4$)alkyl or a (C2 to C$_6$)alkenyl;
the group R$^2$ is H, a linear or branched (C$_1$ to C$_6$)alkyl, a (C$_1$ to C$_6$)alkenyl, a substituted or unsubstituted phenyl (C$_1$ to C$_4$)alkyl, an acetyl, benzoyl or arylsufonyl, a (C$_1$ to C$_7$)alkoxycarbonyl, —OCOCH$_2$CH=CH$_2$, a (C$_3$ to C$_8$)cyclo(C$_1$ to C$_8$)alkoxycarbonyl, —OCOCH$_2$C$_6$H$_5$ or a substituted arylalkoxycarbonyl wherein the substituent is a halogen, a nitro group, an amino group or a methoxyl group;
or the groups R$^1$ and R$^2$ taken together form, with the nitrogen to which they are attached, a 5 to 7 membered ring; and
the groups L$^1$ and L2 are, independently, a linear or branched chain alkyl of the formula —(C$_n$H$_{2n}$)— wherein n is 1 to 8; cycloalkyl of 3 to 8 carbon atoms, or an interphenylene.

7. The method as in claim 5, wherein the animal is a livestock animal.

8. The method of claim 5, wherein the animal is human.

9. A method of treating or preventing weight loss associated with disease in an mammal, comprising administering an amount of a compound of Formula I

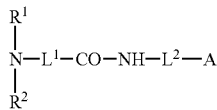
(I)

wherein:
the group A is $SO_3H$ or a pharmaceutically acceptable salt thereof or physiologically hydrolyzable derivative thereof;
the group $R^1$ is H, a linear or branched lower alkyl, an arylalkyl or an alkenyl;
the group $R^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;
or the groups $R^1$ and $R^2$ taken together form, with the nitrogen to which they are attached, a 5 to 7 membered ring; and
the groups $L^1$ and $L^2$ are, independently, a hydrocarbon linking group, a cycloalkyl, or an interphenylene;
with the proviso that the compound of formula I is not beta-alethine;
which amount is sufficient to treat or prevent weight loss.

10. The method of claim 9 wherein the group A is $SO_3H$ or a pharmaceutically acceptable salt thereof or physiologically hydrolyzable ($C_1$ to $C_4$)alkyl or arylalkyl ester thereof;
the group $R^1$ is H, a linear or branched ($C_1$ to $C_6$)alkyl, a substituted or unsubstituted phenyl($C_1$ to $C_4$)alkyl or a (C2 to $C_6$)alkenyl;
the group $R^2$ is H, a linear or branched ($C_1$ to $C_6$)alkyl, a ($C_1$ to $C_6$)alkenyl, a substituted or unsubstituted phenyl ($C_1$ to $C_4$)alkyl, an acetyl, benzoyl or arylsufonyl, a ($C_1$ to $C_7$)alkoxycarbonyl, —$OCOCH_2CH$=$CH_2$, a ($C_3$ to $C_8$)cyclo($C_1$ to $C_8$)alkoxycarbonyl, —$OCOCH_2C_6H_5$ or a substituted arylalkoxycarbonyl wherein the substituent is a halogen, a nitro group, an amino group or a methoxyl group;
or the groups $R^1$ and $R^2$ taken together form, with the nitrogen to which they are attached, a 5 to 7 membered ring; and
the groups $L^1$ and $L^2$ are, independently, a linear or branched chain alkyl of the formula —$(C_nH_{2n})$— wherein n is 1 to 8; cycloalkyl of 3 to 8 carbon atoms, or an interphenylene.

11. A method of treating cachexia in an animal, comprising administering an amount of a compound of Formula I

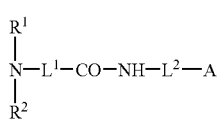
(I)

wherein:
the group A is $SO_3H$ or a pharmaceutically acceptable salt thereof or physiologically hydrolyzable derivative thereof,
the group $R^1$ is H, a linear or branched lower alkyl, an arylalkyl or an alkenyl;
the group $R^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;
or the groups $R^1$ and $R^2$ taken together form, with the nitrogen to which they are attached, a 5 to 7 membered ring; and
the groups $L^1$ and $L^2$ are, independently, a hydrocarbon linking group, a cycloalkyl, or an interphenylene;
with the proviso that the compound of formula I is not beta-alethine;
which amount is sufficient to treat or prevent cachexia in an animal.

12. The method of claim 11 wherein the group A is $SO_3H$ or a pharmaceutically acceptable salt thereof or physiologically hydrolyzable ($C_1$ to $C_4$)alkyl or arylalkyl ester thereof;
the group $R^1$ is H, a linear or branched ($C_1$ to $C_6$)alkyl, a substituted or unsubstituted phenyl($C_1$ to $C_4$)alkyl or a (C2 to $C_6$)alkenyl;
the group $R^2$ is H, a linear or branched ($C_1$ to $C_6$)alkyl, a ($C_1$ to $C_6$)alkenyl, a substituted or unsubstituted phenyl ($C_1$ to $C_4$)alkyl, an acetyl, benzoyl or arylsufonyl, a ($C_1$ to $C_7$)alkoxycarbonyl, —$OCOCH_2CH$=$CH_2$, a ($C_3$ to $C_8$)cyclo($C_1$ to $C_8$)alkoxycarbonyl, —$OCOCH_2C_6H_5$ or a substituted arylalkoxycarbonyl wherein the substituent is a halogen, a nitro group, an amino group or a methoxyl group;
or the groups $R^1$ and $R^2$ taken together form, with the nitrogen to which they are attached, a 5 to 7 membered ring; and
the groups $L^1$ and $L^2$ are, independently, a linear or branched chain alkyl of the formula —$(C_nH_{2n})$— wherein n is 1 to 8; cycloalkyl of 3 to 8 carbon atoms, or an interphenylene.

13. The method of claim 9 wherein the disease is anorexia nervosa, bulimia, AIDS, cancer, or Crohn's disease.

14. A method of decreasing mortality among a population of livestock animals, comprising administering to the animal an amount of a compound of Formula I

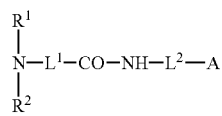
(I)

wherein:
the group A is $SO_3H$ or a pharmaceutically acceptable salt thereof or physiologically hydrolyzable derivative thereof;
the group $R^1$ is H, a linear or branched lower alkyl, an arylalkyl or an alkenyl;
the group $R^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;
or the groups $R^1$ and $R^2$ taken together form, with the nitrogen to which they are attached, a 5 to 7 membered ring; and the groups $L^1$ and $L^2$ are, independently, a hydrocarbon linking group, a cycloalkyl, or an interphenylene;

with the proviso that the compound of formula I is not beta-alethine;

which amount is sufficient to decrease mortality in the population of livestock animals.

15. A method of improving feed efficiency in an animal, comprising administering to the animal an amount of a compound of Formula I

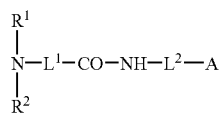

(I)

wherein:

the group A is SO$_3$H or a pharmaceutically acceptable salt thereof or physiologically hydrolyzable derivative thereof;

the group R$^1$ is H, a linear or branched lower alkyl, an arylalkyl or an alkenyl;

the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;

or the groups R$^1$ and R$^2$ taken together form, with the nitrogen to which they are attached, a 5 to 7 membered ring; and the groups L$^1$ and L$^2$ are, independently, a hydrocarbon linking group, a cycloalkyl, or an interphenylene;

with the proviso that the compound of formula I is not beta-alethine;

which amount is sufficient to improve feed efficiency in the animal.

16. A method of increasing the ability of an animal to withstand environmental stressors selected from the group consisting of food deprivation, temperature changes and exposure to one or more pathogens, comprising administering to the animal an amount of a compound of Formula I

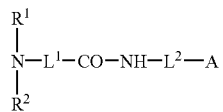

(I)

wherein:

the group A is SO$_3$H or a pharmaceutically acceptable salt thereof or physiologically hydrolyzable derivative thereof;

the group R$^1$ is H, a linear or branched lower alkyl, an arylalkyl or an alkenyl;

the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;

or the groups R$^1$ and R$^2$ taken together form, with the nitrogen to which they are attached, a 5 to 7 membered ring; and the groups L$^1$ and L$^2$ are, independently, a hydrocarbon linking group, a cycloalkyl, or an interphenylene;

with the proviso that the compound of formula I is not beta-alethine;

which amount is sufficient to enable the animal to withstand environmental stressors.

17. The method of claim 16, wherein the environmental stress is food deprivation.

18. The method of claim 16, wherein the environmental stress is temperature change.

19. The method of claim 16, wherein the environmental stress is exposure to one or more pathogens.

20. A method of increasing production of a desired product selected from the group consisting of milk, meat, wool, caviar, feathers, fur and hoofs, by an animal, comprising administering to the animal an amount of a compound of Formula I

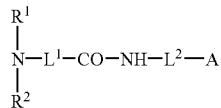

(I)

wherein:

the group A is SO$_3$H or a pharmaceutically acceptable salt thereof or physiologically hydrolyzable derivative thereof;

the group R$^1$ is H, a linear or branched lower alkyl, an arylalkyl or an alkenyl;

the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;

or the groups R$^1$ and R$^2$ taken together form, with the nitrogen to which they are attached, a 5 to 7 membered ring; and the groups L$^1$ and L$^2$ are, independently, a hydrocarbon linking group, a cycloalkyl, or an interphenylene;

with the proviso that the compound of formula I is not beta-alethine;

which amount is sufficient to increase production of a desired product.

21. The method of claim 16, wherein the bird is a chicken.

22. The method of claim 21, wherein the compound is administered in ovo.

23. The method of claim 21, wherein the compound is administered subcutaneously.

24. A method of preventing one or more bacterial or viral diseases in an animal raised in crowded living conditions, comprising administering to the animal an amount of a compound of Formula I

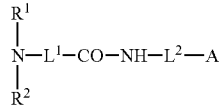

(I)

wherein:

the group A is SO$_3$H or a pharmaceutically acceptable salt thereof or physiologically hydrolyzable derivative thereof, the group R$^1$ is H, a linear or branched lower alkyl, an arylalkyl or an alkenyl;

the group R$^2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl;

or the groups $R^1$ and $R^2$ taken together form, with the nitrogen to which they are attached, a 5 to 7 membered ring; and the groups $L^1$ and $L^2$ are, independently, a hydrocarbon linking group, a cycloalkyl, or an interphenylene;

with the proviso that the compound of formula I is not beta-alethine;

which amount is sufficient to prevent one or more of said diseases.

25. The method as in claim 24, wherein the compound is carbobenzoxy beta-alanyl taurine.